(12) United States Patent
Shimizu (10) Patent No.: US 7,901,643 B2
(45) Date of Patent: Mar. 8, 2011

(54) FLOW CHANNEL DEVICE AND SENSOR UNIT FOR ASSAY IN UTILIZING ATTENUATED TOTAL REFLECTION

(75) Inventor: Hitoshi Shimizu, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 1134 days.

(21) Appl. No.: 11/329,129

(22) Filed: Jan. 11, 2006

(65) Prior Publication Data

US 2006/0153742 A1 Jul. 13, 2006

(30) Foreign Application Priority Data

Jan. 11, 2005 (JP) ................................ 2005-004127

(51) Int. Cl.
*B01L 3/00* (2006.01)
(52) U.S. Cl. .......... 422/417; 422/100; 436/180; 356/445
(58) Field of Classification Search .................. 422/100; 436/180; 356/445
See application file for complete search history.

(56) References Cited

U.S. PATENT DOCUMENTS

| | | |
|---|---|---|
| 4,366,241 A | 12/1982 | Tom et al. |
| 4,440,497 A | 4/1984 | Carey et al. |
| 5,064,287 A | 11/1991 | Magnussen, Jr. |
| 5,164,589 A | 11/1992 | Sjödin |
| 5,313,264 A | 5/1994 | Ivarsson et al. |
| 5,443,890 A | 8/1995 | Öhman |
| 6,720,157 B2 * | 4/2004 | Indermuhle et al. ........... 435/7.1 |
| 2002/0034457 A1 | 3/2002 | Reichert et al. |
| 2003/0156292 A1* | 8/2003 | Naya .............................. 356/445 |
| 2005/0046854 A1* | 3/2005 | Kunuki et al. ................. 356/445 |

FOREIGN PATENT DOCUMENTS

| | | |
|---|---|---|
| EP | 1 324 019 A1 | 7/2003 |
| EP | 1 512 961 A1 | 3/2005 |
| JP | 57-63454 A | 4/1982 |
| JP | 3294605 B2 | 4/2002 |

* cited by examiner

*Primary Examiner* — Jill Warden
*Assistant Examiner* — Shogo Sasaki
(74) *Attorney, Agent, or Firm* — Sughrue Mion, PLLC (57) ABSTRACT

A sensor unit for use in a surface plasmon resonance (SPR) assay includes a flow channel device, which causes a sample fluid of a sample to flow on a sensing surface lying on a prism. The flow channel device includes a rigid device body part having an opposing surface positioned opposite to the sensing surface. A flow recess is formed in the opposing surface, closed by the prism to constitute a flow channel, for covering the sensing surface. A sealant portion is overlaid on an edge portion of the opposing surface and the flow recess in the device body part. The sealant portion tightens closing between the device body part and the prism. Also, the sealant portion projects over the opposing surface of the device body part in a state before contacting the prism. In addition, the sealant portion is formed from material having a small non-specific adsorption.

10 Claims, 6 Drawing Sheets

FLOW CHANNEL DEVICE AND SENSOR UNIT FOR ASSAY IN UTILIZING ATTENUATED TOTAL REFLECTION

BACKGROUND OF THE INVENTION

1. Field of the Invention

The present invention relates to a flow channel device and sensor unit for assay in utilizing attenuated total reflection. More particularly, the present invention relates to a flow channel device and sensor unit for assay in utilizing attenuated total reflection, in which a sensing surface can be positioned precisely relative to a flow channel for flow of a sample fluid.

2. Description of the Related Art

An assay apparatus for assay in utilizing attenuated total reflection is used for various kinds of studies in a biochemical field or the like, for example to study interaction of protein, DNA and various biomaterials, and to select candidate drugs by screening. Also, the technique is useful in the fields of the clinical medicine, food industries and the like.

A surface plasmon resonance (SPR) sensor is known as an assay apparatus in utilizing attenuated total reflection. Surface plasmon is a term to mean the compressional wave created on the surface of the metal and included in plasmon as quantized expression of the compressional wave. Free electrons in a metal vibrate to generate the compressional wave.

U.S. Pat. Nos. 5,164,589 and 5,313,264 (corresponding to JP-B 3294605) disclose an SPR assay apparatus in which an optical system of Kretschmann configuration is used for incidence of light to the metal film. According to the Kretschmann configuration, the thin film/dielectric interface of the metal film is fitted on a prism, which condenses light and directs the light to the thin film/dielectric interface in a manner conditioned for total reflection.

Upon the total reflection created on the metal/dielectric interface, a small component of the light passes through the metal film without reflection, and penetrates to the sensing surface. A wave of the penetrating component is called an evanescent wave. Surface plasmon resonance (SPR) is created when frequency of the evanescent wave coincides with that of the surface plasmon. In response to this, intensity of the reflected light attenuates remarkably. In the assay apparatus, the attenuation in the reflected light reflected by the metal/dielectric interface is detected, to recognize creation of the SPR on the sensing surface.

A sample or biomaterial, such as protein and DNA, are handled as sample fluid for the purpose of preventing deactivation or modification due to drying. The sample fluid contains biomaterial and fluid medium, examples of which include pure water, physiological saline water, liquid buffer and the like. The U.S. Pat. No. 5,164,589 and U.S. Pat. No. 5,313,264 disclose the assay apparatus for analyzing interaction of the sample. The assay apparatus has a flow channel for flowing and introducing the sample fluid on to a sensing surface. Also, a linker film is overlaid inside the flow channel to have the sensing surface, for immobilizing the sample. Ligand fluid is introduced to the flow channel for immobilizing the ligand on the sensing surface. After this, analyte fluid is introduced for contact of the analyte and the ligand, to assay the interaction between those.

The assay apparatus of U.S. Pat. No. 5,164,589 and U.S. Pat. No. 5,313,264 includes an assay stage where a prism and a flow channel are disposed. A sensor unit of a chip type is positioned on the assay stage for the measuring step, the sensor unit including a glass support and a thin film of metal overlaid thereon.

A problem in the immobilization is in that time required from the introduction of the ligand until completion of the immobilization is as long as one (1) hour or so. This is remarkably longer than the measuring step for the assay which can take only a small number of minutes. As the assay stage of U.S. Pat. No. 5,164,589 and U.S. Pat. No. 5,313,264 is used for both of the sample immobilizing flow and the measuring step for the assay, the assay stage must be occupied for the immobilization during the assay. Other sensor units cannot be set on the assay stage. This is a problem of delay in the operation on the assay stage.

It is conceivable to immobilize samples for all of plural sensor units before assay of those, for the purpose of raising efficiency. However, there is a drawback in that the sensing surface will be dried to deactivate the samples, or will receive impurity stuck thereto, particularly after storing the sensor units with immobilized samples. No assay with precision is possible.

In view of this, an SPR sensor unit is conceived, including a flow channel block, a prism and a retaining block. The flow channel block has a flow channel. The prism is overlaid with a thin film of metal. The retaining block keeps the flow channel block positioned on the prism by setting the flow channel at the thin film.

According to the conception, the flow channel and the prism are provided in the sensor unit itself. The immobilization and the assay are made in simultaneously sequences for plural sensor units, so as to raise efficiency in the operation. Also, the disposition of the flow channel allows preserving of the sensor unit with the sample fluid as storage after the immobilization. Drying of the sensing surface can be prevented.

The flow channel block is formed from rubber or other elastic material for tight contact with the thin film of metal. A retaining block presses the flow channel block against the thin film and kept deformed resiliently. However, no known technique can eliminate offsetting of the flow channel relative to the sensing surface, because a control of an amount of the deformation is extremely difficult.

If the linker film with the sensing surface is offset from the flow channel, an area defined by facing of those changes. Thus, an amount of immobilized ligand changes to influence precision in the measuring step. Also, the shape of the flow channel is likely to change. A flow rate of a fluid of a sample changes to lower the precision in the measuring step.

SUMMARY OF THE INVENTION

In view of the foregoing problems, an object of the present invention is to provide a flow channel device and sensor unit for assay in utilizing attenuated total reflection, in which a sensing surface can be positioned precisely relative to a flow channel for flow of a sample fluid.

In order to achieve the above and other objects and advantages of this invention, a flow channel member causes a sample fluid of a sample to flow on a sensing surface lying on a first surface. The flow channel member includes a rigid device body part having an opposing surface positioned opposite to the sensing surface. A flow recess is formed in the opposing surface, closed by the first surface to constitute a flow channel, for covering the sensing surface. A rigid device body part is formed from a rigid material, for constituting a component including the flow channel. A sealant portion is formed from a soft elastic material having a higher softness than the rigid material, disposed on an edge of the flow recess, for sealing the flow recess by contacting the first surface.

Preferably, a soft elastic layer is overlaid on an edge portion of at least the opposing surface or the flow recess in the device body part, and has a higher softness than the device body part.

Preferably, the soft layer includes a sealant for tightening closing between the device body part and the first surface.

Preferably, the flow channel and the sensing surface are adapted to assay of the sample by utilizing attenuated total reflection, and the first surface is constituted by a prism.

Preferably, the soft layer projects over the opposing surface of the device body part in a state before contacting the first surface.

Preferably, the soft layer is disposed to spread on an inner surface of the flow channel.

Preferably, a projecting sealant portion of the soft layer in contact with the first surface has a thickness equal to or more than 0.1 mm and equal to or less than 1.0 mm.

Furthermore, first and second orifices are formed in the device body part to extend from first and second ends of the flow recess, for shaping the flow channel in a substantially U-shape.

Preferably, the soft layer is formed from an elastic plastic material.

Preferably, the soft layer is formed from material having a small non-specific adsorption.

Preferably, the device body part and the soft layer are formed together by two color molding.

In a preferred embodiment, the device body part and the soft layer are obtained together by insert molding.

Preferably, the device body part is produced from a rigid plastic material or a metal.

Preferably, the rigid plastic material is crystalline polyolefin.

Preferably, the elastic plastic material is elastomer.

Preferably, the elastomer is amorphous polyolefin elastomer.

Also, a sensor unit is provided, having a prism, a thin film including a first surface and a sensing surface, the first surface being connected with the prism to constitute an interface, the interface attenuating intensity of reflected illuminating light upon receiving application of the illuminating light in a form satisfying a total reflection condition, and a flow channel device, associated with the prism, for causing a sample fluid of a sample to flow on the sensing surface, wherein when the sample in the sample fluid contacts the sensing surface, an angle of incidence of the illuminating light upon occurrence of attenuation is changed according to reaction of the sample. The sensor unit includes a rigid device body part having an opposing surface positioned opposite to the sensing surface. A flow recess is formed in the opposing surface, closed by the prism to constitute a flow channel, for covering the sensing surface. A soft elastic layer is overlaid on an edge portion of at least the opposing surface or the flow recess in the device body part, and has a higher softness than the device body part.

Furthermore, a fastener keeps the prism in contact with the flow channel device.

Preferably, the fastener squeezes the flow channel device and also engages with the prism.

In a preferred embodiment, the fastener includes a fastening projection, formed to project from the flow channel device, for engagement with the prism.

Consequently, a sensing surface can be positioned precisely relative to a flow channel for flow of a sample fluid, because the soft elastic layer can keep connection with the device body part in a acceptably tight manner.

BRIEF DESCRIPTION OF THE DRAWINGS

The above objects and advantages of the present invention will become more apparent from the following detailed description when read in connection with the accompanying drawings, in which.

DETAILED DESCRIPTION OF THE PREFERRED EMBODIMENT(S) OF THE PRESENT INVENTION

Figure 1:
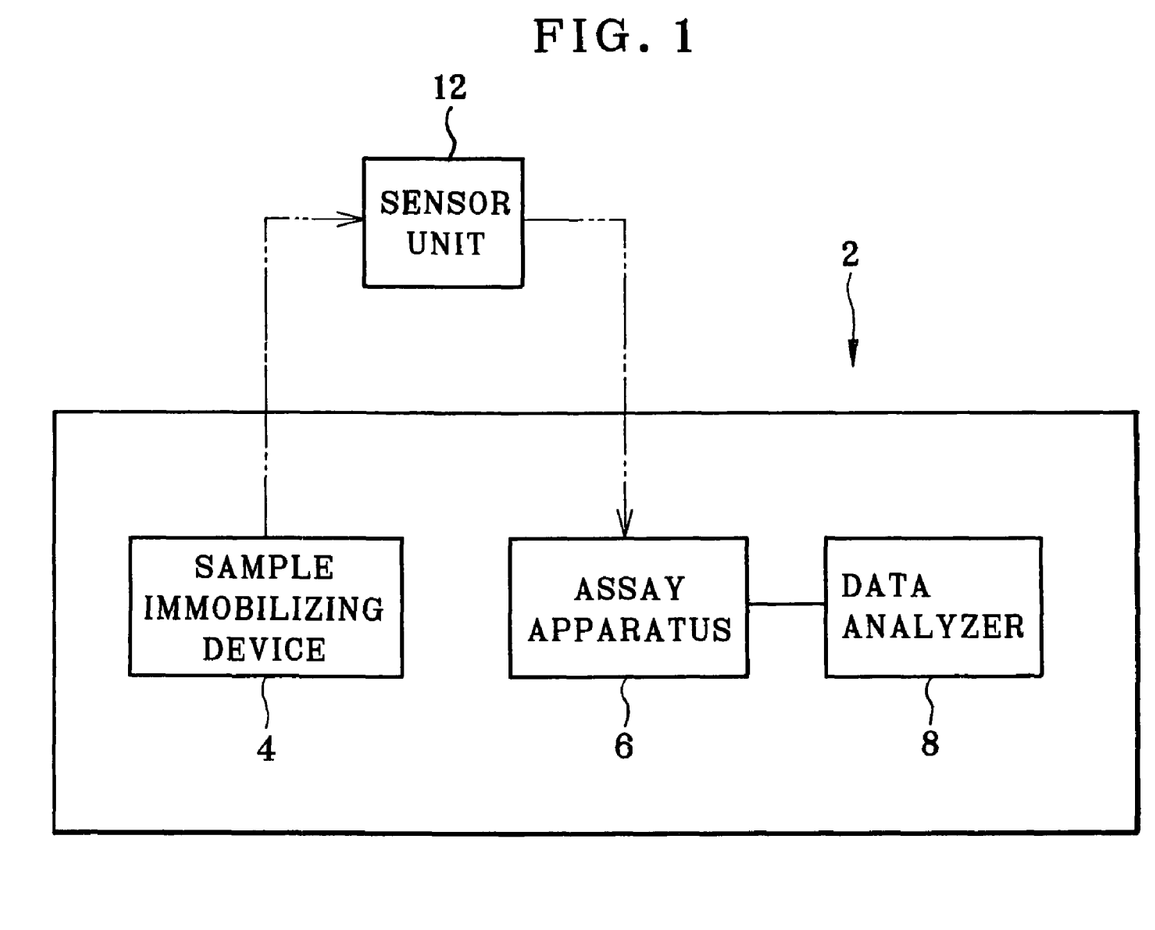
FIG. 1 is a block diagram illustrating a surface plasmon resonance assay system.

In FIG. 1, a surface plasmon resonance (SPR) assay system 2 is schematically illustrated. The assay system 2 includes a sample immobilizing device 4, an assay apparatus 6 and a data analyzer 8. The sample immobilizing device 4 introduces fluid of ligand toward a sensing surface for the purpose of immobilizing the ligand. The assay apparatus 6 assays interaction between the ligand and an analyte introduced after the ligand immobilization. The data analyzer 8 is provided with data from the assay apparatus 6, and analyzes the data. A sensor unit 12 is separated from any components of the assay system 2, and adapted to operation of a sample immobilizing flow and assay. This can makes it easy to measure a plurality of samples in a rapid manner.

Figure 2:
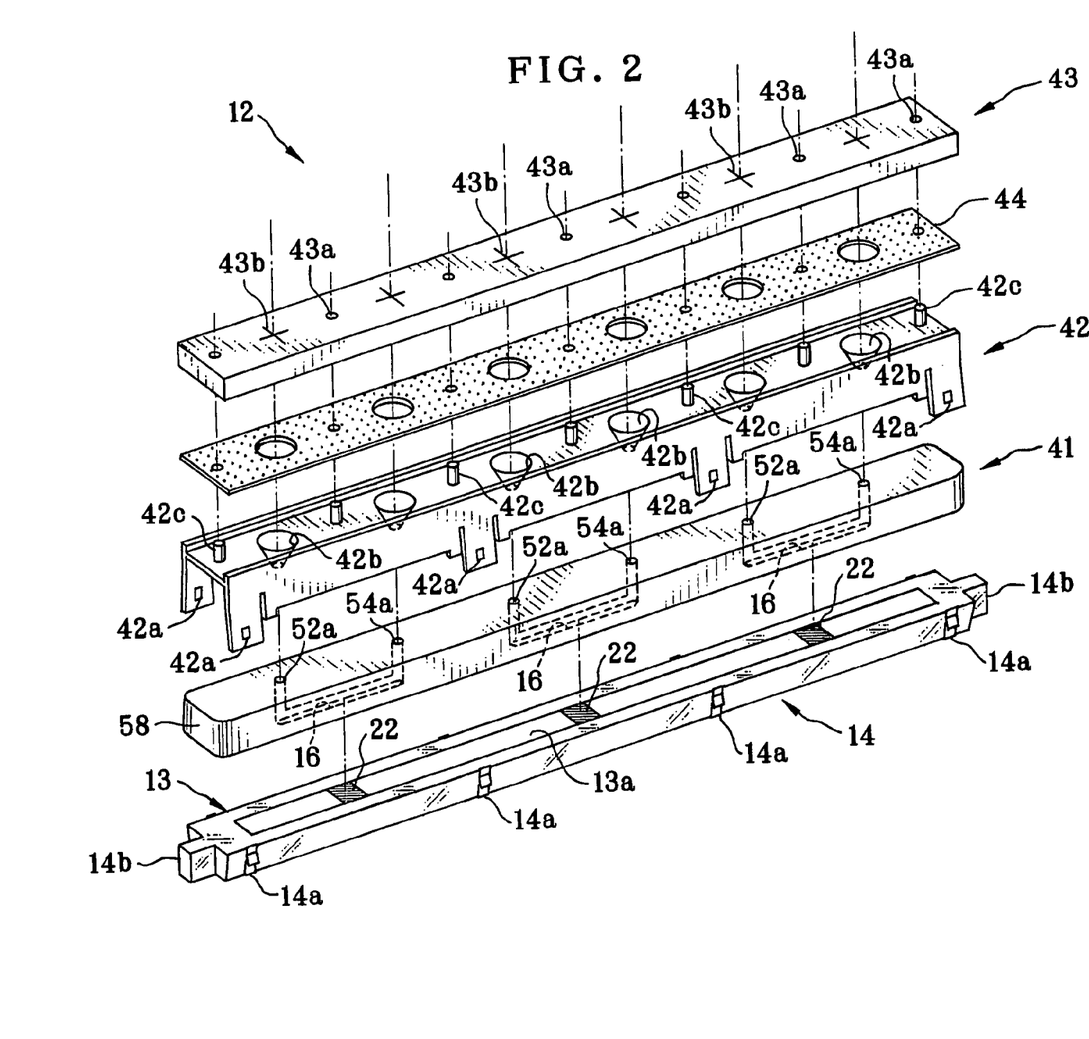
FIG. 2 is an exploded perspective illustrating a sensor unit in which a flow channel device is included.

In FIG. 2, elements in the sensor unit 12 are illustrated. The sensor unit 12 includes a prism 14 constituting a first panel, a thin film 13 and a flow channel device 41 or multi-channel flow cell. The prism 14 is overlaid with the thin film 13 on which biomaterial for assay is positioned. The flow channel device 41 includes a flow channel 16, which causes fluid of the biomaterial to flow on to the thin film 13. A fastener block 42 retains the flow channel device 41 by keeping a lower face of the flow channel device 41 pressed on an upper face of the prism 14. A lid 43 is secured on an upper surface of the fastener block 42.

Figure 3:
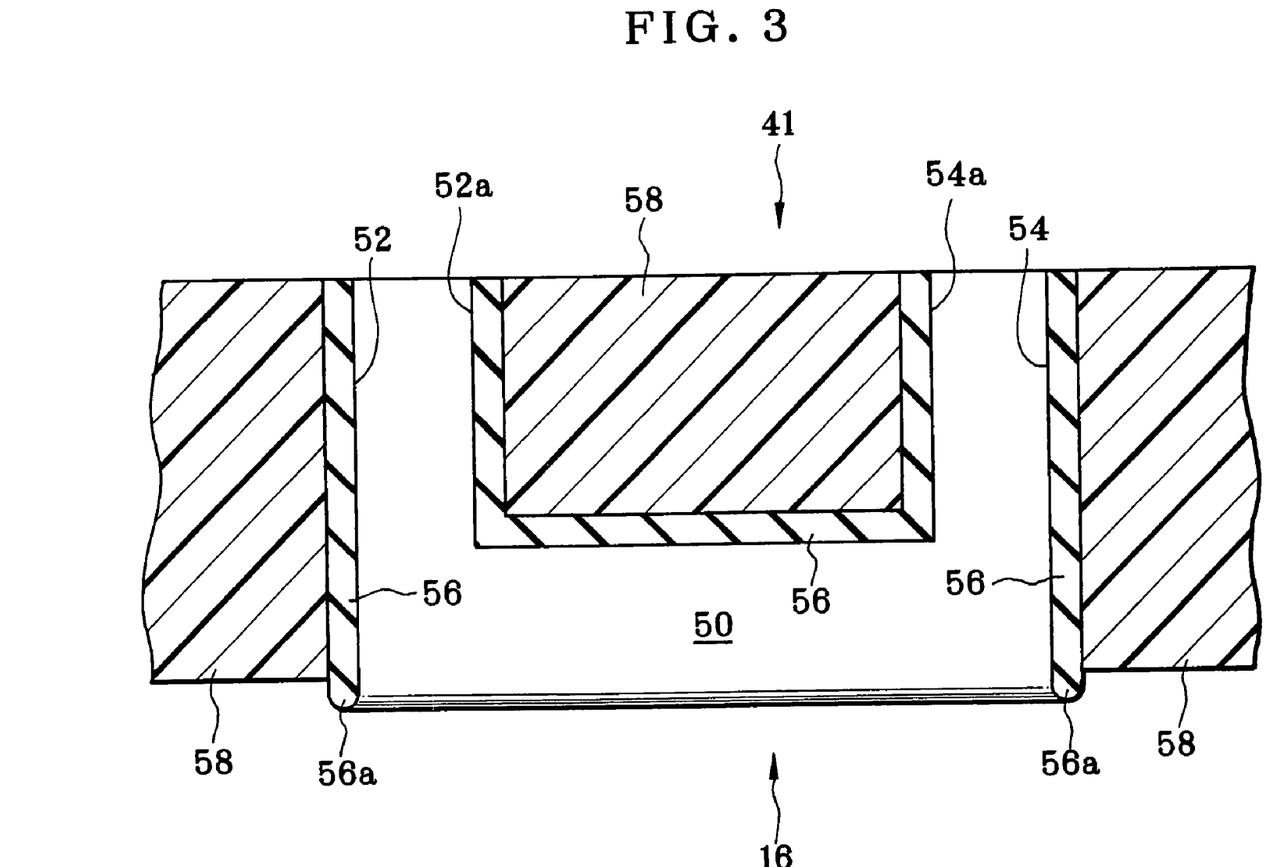
FIG. 3 is a cross section illustrating the flow channel device.

The flow channel device 41 is a molded piece and long in one direction, and has three flow channels 16 arranged in the longitudinal direction. In FIG. 3, the flow channels 16 are in the U shape, and respectively include a flow recess 50, an entrance zone 52, and an exit zone 54. A lower surface of the flow channel device 41 is an opposing surface opposed to an upper surface of the prism 14, the upper surface being a prism surface. The flow recess 50 is formed in a lower surface of the flow channel device 41, and closed by an upper surface of the prism 14 when set on the prism 14. The entrance zone 52 and the exit zone 54 come through the flow channel device 41 and extend from ends of the flow recess 50 vertically or in a direction crosswise to the longitudinal direction of the flow recess 50. An entrance orifice 52a opens at the end of the entrance zone 52. An exit orifice 54a opens at the end of the exit zone 54.

The flow channels 16 have a diameter of approximately 1 mm. An interval between the entrance orifice 52a and the exit orifice 54a or the length of the flow recess 50 is approximately 10 mm. A lower side of the flow channels 16 where the flow recess 50 is open is enclosed by the prism 14 having the thin film 13. There are defined sensor cells 17 each of which is a portion of the thin film 13 closed by the portion about the recess. See FIG. 4. In the present embodiment, the number of the sensor cells 17 is three. However, the sensor unit 12 may have one or two sensor cells, or four or more of the sensor cells 17.

The flow channel device 41 includes a rigid device body part 58 and a soft and elastic layer or coat 56. The device body part 58 is formed from a rigid material. The soft elastic layer 56 is formed from a soft and elastic material having a higher softness than the device body part 58 and having elasticity. The device body part 58 constitutes a main part of the flow channel device 41 having the flow channel 16. The soft elastic layer 56 constitutes a layer for coating the entirety of the inner surface of the flow recess 50 and the flow channel 16. The layer receives each of the fluid dispenser 19 of the sample immobilizing device 4 and the fluid dispenser 26 of the assay apparatus 6 when such is inserted in the entrance zone 52 and the exit zone 54.

Also, a projecting sealant portion 56a is one portion of the soft elastic layer 56 and is overlaid on an edge of the flow recess 50. The projecting sealant portion 56a extends about the open end of the flow recess 50 to an amount of its entire circumference. The projecting sealant portion 56a projects down from a lower case of the flow channel device 41, and seals the inside of the flow recess 50 by contacting the upper face of the prism 14. When the flow channel device 41 is pressed on the prism 14 by the fastener block 42, the projecting sealant portion 56a is elastically deformed to tighten the contact with the thin film 13. The projecting sealant portion 56a closes the flow recess 50 in a fluid tight manner with the prism 14. A thickness of the soft elastic layer 56 can be preferably equal to or more than 0.1 mm and equal to or less than 1.0 mm. Should it be smaller than 0.1 mm, the fluid-tight effect of the soft elastic layer 56 may be too small due to its easy deformation. Should it be greater than 1.0 mm, offsetting of the soft elastic layer 56 may be unacceptably excessive. An depth or amount of protrusion of the projecting sealant portion 56a can be approximately 0.1 mm in consideration of its elasticity.

In the course of the manufacture of the flow channel device 41, the soft elastic layer 56 and the device body part 58 included in the flow channel device 41 are produced by the two color molding, namely double molding, in which two materials are molded at the same time in the same mold set.

The soft elastic layer 56 contacts the sample fluid flowing in the flow channel 16 because overlaid on the inner wall of the flow channel 16. Adsorption of samples contained in the sample fluid should be prevented in view of the required contact of the soft elastic layer 56 with the sample fluid. Thus, it is preferable that the material characteristically has a small non-specific adsorption. Examples of the materials for the soft elastic layer 56 on the device body part 58 include elastic resins having small non-specific adsorption, such as amorphous polyolefin elastomer. Examples of the hard materials for the device body part 58 include crystalline polyolefin, such as polypropylene.

In FIG. 2, the thin film 13 of a strip shape is positioned at the flow channel 16 and formed on a surface of the prism 14 by vapor deposition. An example of material for the thin film 13 is gold (Au) or silver (Ag). A thickness of the thin film 13 is 50 nm. The thickness can be changed for the suitability in view of the material of the thin film 13, a wavelength of light to be applied, and the like.

A linker film 22 is overlaid on the thin film 13 and positioned at the flow channel 16 of the sensor cells 17 for immobilizing ligand. A sensing surface 13a lying on the first panel is one of the surfaces of the thin film 13 where the linker film 22 appears an obverse surface. An interface 13b is a remaining one of the surfaces of the thin film 13 connected with the prism 14. The prism 14 condenses light traveling toward the interface 13b. The thin film 13, upon incidence of the interface 13b by satisfying a total reflection condition, generates surface plasmon resonance (SPR) on the sensing surface 13a.

Fastening claws 14a are formed to project from the prism 14 at its sides as viewed longitudinally. Fastening portions 42a of the fastener block 42 are engageable with the fastening claws 14a. The flow channel device 41 as a multi-channel flow cell is sandwiched between the fastener block 42 and the prism 14. A lower surface of the flow channel device 41 is kept fitted on the prism 14. Retaining projections 14b protrude from ends of the prism 14 as viewed in its longitudinal direction. A sensor holder (not shown) contains a plurality of sensor units 12. The retaining projections 14b are formed for positioning the sensor unit 12 in a contained state by engagement with the sensor holder.

Various materials can be used for forming the prism 14, their examples including optical glasses, such as borosilicate crown (BK7) glass, barium crown (Bak4) glass, and the like; and optical plastic materials, such as polymethyl methacrylate (PMMA), polycarbonate (PC), amorphous polyolefin (APO) and the like.

An access hole 42b is formed in the fastener block 42, and positioned at each of the entrance orifice 52a and the exit orifice 54a of the flow channel 16, for entry of an end of each of dispensing and removing pipettes and the like. The access hole 42b has a funnel shape for introducing liquid ejected by the pipettes toward the entrance orifice 52a. When the fastener block 42 becomes engaged with the prism 14 together with the flow channel device 41, a lower face of the access hole 42b becomes connected with the entrance orifice 52a and the exit orifice 54a of the flow channel 16 for flow of fluid.

Rod shaped bosses 42c are formed to project beside the access hole 42b. Holes 43a are formed in the lid 43. The bosses 42c are fitted in the holes 43a, to position the lid 43 firmly. Double sided adhesive tape 44 attaches the lid 43 to an upper surface of the fastener block 42. Note that suitable holes are formed in the double sided adhesive tape 44, and associated with the access hole 42b and the bosses 42c.

The lid 43 covers the access hole 42b communicating to the flow channel 16, and prevents evaporation of liquid in the flow channel 16. The lid 43 is formed from rubber, elastomer, resin or other elastic material. A cross shaped access slit 43b is formed in the lid 43 and positioned respectively at the access hole 42b. The cross shaped access slit 43b is formed to enable insertion of pipettes. When the pipette is externally pulled out, the cross shaped access slit 43b elastically closes the access hole 42b again by returning to its initial state.

Figure 4:
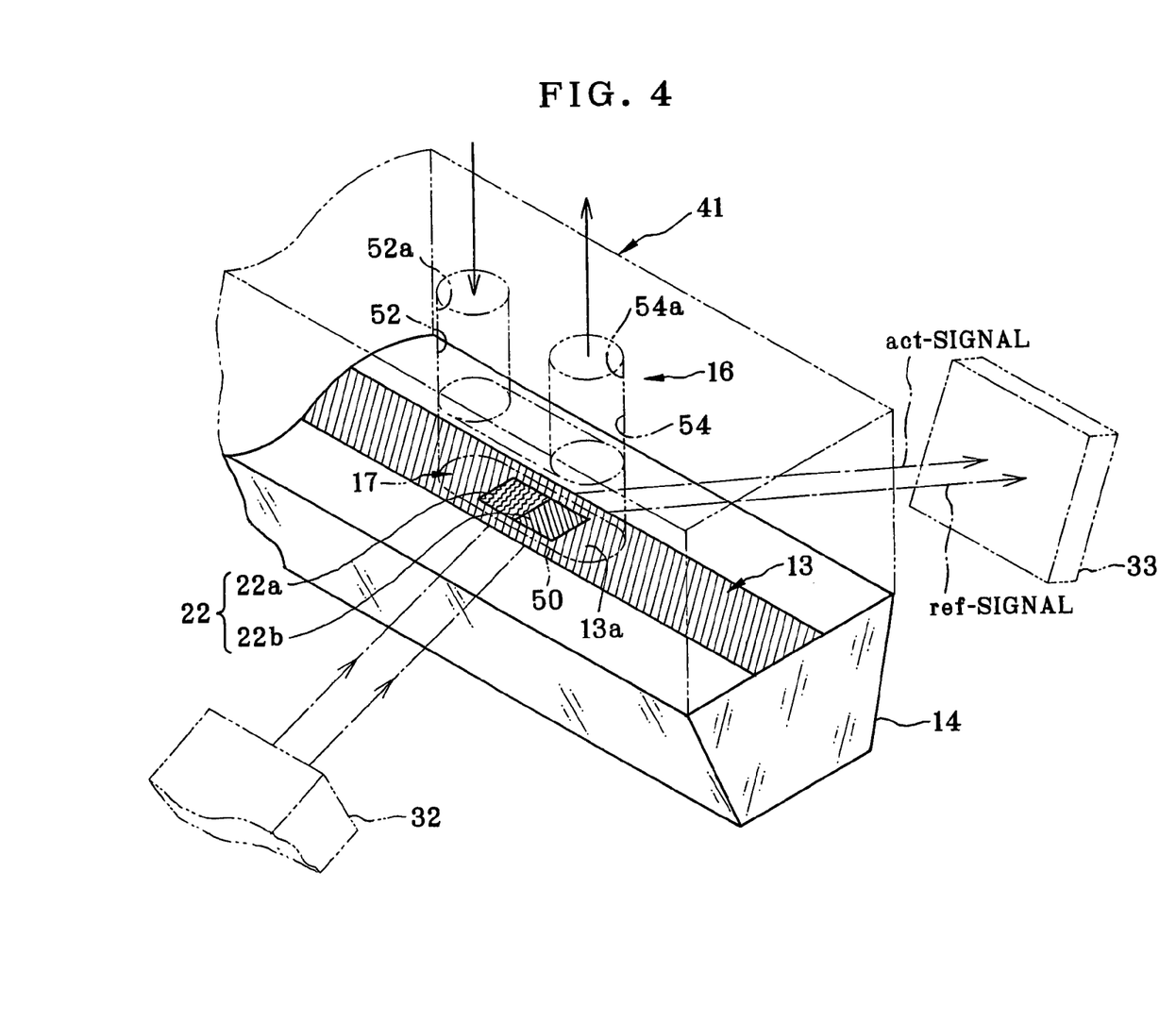
FIG. 4 is a perspective view illustrating the sensor unit together with an optical assay unit.

In FIG. 4, the linker film 22 on the thin film 13 is depicted. There are a measuring region 22a (act) and a reference region 22b (ref) formed in the linker film 22. The measuring region 22a has immobilization of a ligand, and is a region for reaction between the ligand and analyte. The reference region 22b does not have immobilization of a ligand, and is used for outputting a reference signal for comparison with a signal retrieved from the measuring region 22a. Note that the reference region 22b is formed in the course of film production of the linker film. An example of a process of the forming has steps of surface processing of the linker film 22 at first, and then deactivating the reaction groups in approximately a half of an entire area of the linker film 22 for binding with ligand. Thus, a half of the linker film 22 becomes the measuring region 22a. A remaining half of the linker film 22 becomes the reference region 22b.

Figure 5A:
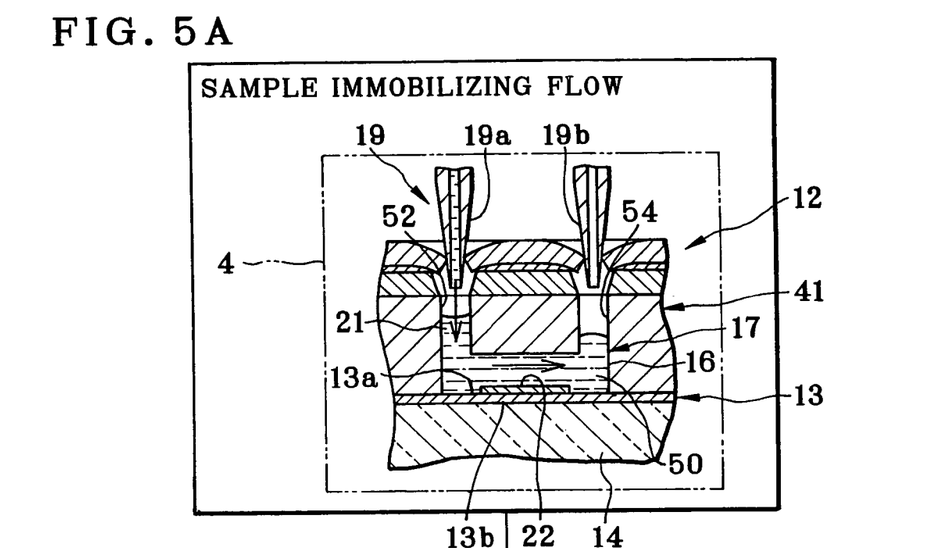
FIG. 5A is an explanatory view in section, illustrating a process of a sample immobilizing flow.
Figure 5B:
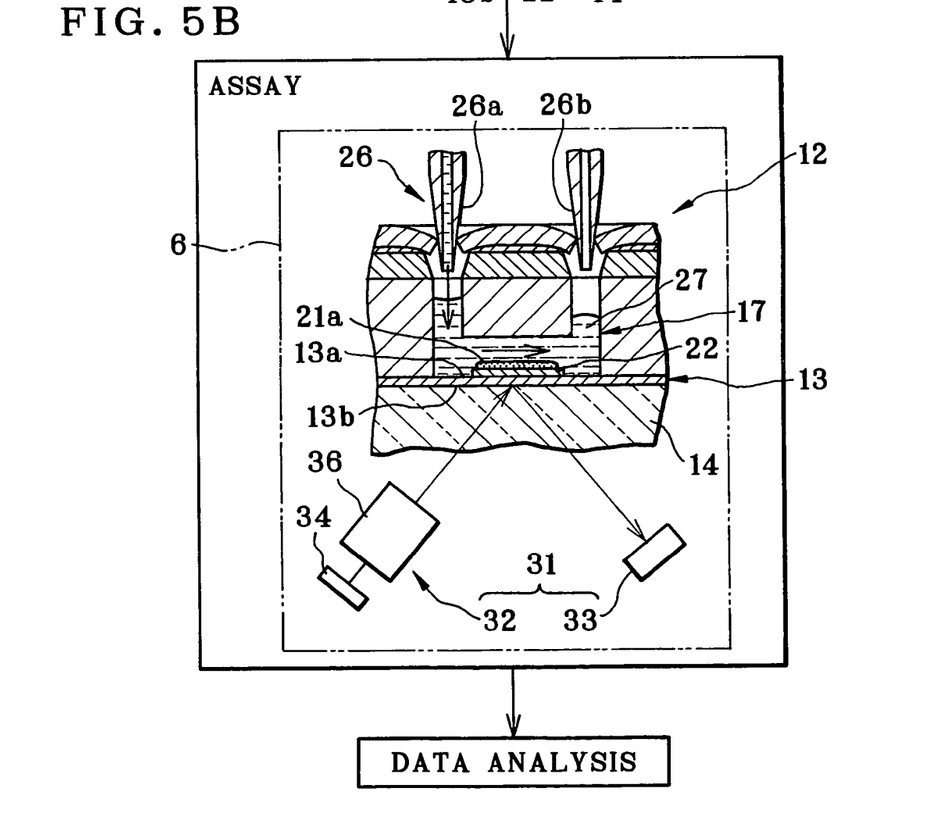
FIG. 5B is an explanatory view in section, illustrating processes of assay and data analysis.

FIGS. 5A and 5B are now referred to for describing assay operation according to the SPR.

A sample immobilizing flow is for binding of ligand on the sensing surface 13a of the linker film 22. At first, the sensor unit 12 is set in the sample immobilizing device 4. The fluid dispenser 19 is included in the sample immobilizing device 4, and has a dispensing pipette tip 19a and a draining pipette tip 19b. The dispensing pipette tip 19a is set at the entrance orifice 52a. The draining pipette tip 19b is set at the exit orifice 54a. The dispensing pipette tip 19a introduces fluid to the flow channel 16. The draining pipette tip 19b sucks and removes fluid from the flow channel 16. The introduction with the dispensing pipette tip 19a is at the same time as the removal with the draining pipette tip 19b. Ligand fluid 21 as sample fluid, as a fluid which contains ligand or biomaterial and fluid medium, is introduced through the entrance orifice 52a by the fluid dispenser 19.

In the sample immobilizing device 4, pre-treatment before a ligand immobilizing flow with the ligand fluid 21 is wetting of the linker film 22 by use of liquid buffer, and activation of the linker film 22 for the purpose of facilitating binding of the ligand to the linker film 22. An example of an immobilizing method is the amine coupling method. An example of material for the linker film is carboxy methyl dextran, to bind an amino group contained in the ligand with the dextran directly by a covalent bond. An example of liquid for the activation is mixture of N'-(3-dimethylaminopropyl) carbodiimide hydrochloride (EDC) and N-hydroxy imide succinate (NHS). The sample immobilizing device 4, after the activation, introduces liquid buffer for the ligand immobilizing flow to wash and clean the flow channel 16.

Various liquids are available for use as the liquid buffer for the ligand immobilizing flow, and solvent or diluent for the ligand fluid 21. Examples of the liquids include buffer liquids, or physiological saline water and other aqueous solutions of physiological salts, and pure water. It is possible according to a type of the ligand to determine suitably solution types and pH values of the solutions, and types of substances to be mixed, and their density. If a biomaterial is used as a ligand, physiological saline water is used of which pH value is kept neutralized. In the amine coupling method described above, the linker film 22 is electrified negatively because of the carboxy methyl dextran. In consideration of this, it is possible to use phosphate buffered saline (PBS) solution having strong operation of buffer and containing phosphate salt at high density which is not physiological, because protein can be electrified positively for the purpose of facilitating binding with the linker film 22.

The sample immobilizing device 4, after the activation and washing, introduces the ligand fluid 21 to the flow channel 16 for immobilization. Ligand 21a as sample such as biomaterial diffused in the ligand fluid 21, in introducing the ligand fluid 21, gradually comes near to and binds with the linker film 22. This is the ligand immobilizing flow of the ligand 21a on the linker film 22. It is general that a step of the immobilization requires approximately one (1) hour, during which the sensor unit 12 is preserved in an environment conditioned suitably, for example at a conditioned temperature. Until the immobilization, the ligand fluid 21 in the flow channel 16 may be left to stand in a stationary state. However, the ligand fluid 21 can be preferably stirred or turbulently flowed for ensured fluidity in the flow channel 16. The stirring or turbulent flow can promote binding of the ligand 21a with the linker film 22, to raise an immobilized amount of the ligand 21a.

When the immobilization of the ligand 21a on the linker film 22 is completed, then the sample immobilizing device 4 removes the ligand fluid 21 from the flow channel 16. Namely, the draining pipette tip 19b discharges the ligand fluid 21 by suction. After this, the linker film 22 is washed by introducing washing liquid into the flow channel 16. In the sample immobilizing device 4, a blocking step is made after the washing. A blocking liquid is introduced into the flow channel 16, to deactivate the reaction group remaining without binding with the ligand. A preferable example of the blocking liquid is ethanol amine hydrochloride. After the blocking, the flow channel 16 is washed again. The sample immobilizing device 4 introduces evaporation retardant to the flow channel 16 after the final washing. The sensor unit 12 remains preserved until the assay with the linker film 22 humid on the evaporation retardant.

For the process of the assay, the sensor unit 12 is set in the assay apparatus 6. The assay apparatus 6 includes the fluid dispenser 26 and an optical assay unit 31 for surface plasmon resonance. The fluid dispenser 26 is structurally similar to the fluid dispenser 19 in the sample immobilizing device 4. The optical assay unit 31 applies illuminating light to the sensor unit 12, and also measures interaction between the ligand and analyte. The dispensing pipette tip of the fluid dispenser 26 introduces fluids into the flow channel 16 through the entrance orifice 52a.

The optical assay unit 31 is constituted by an illuminator 32 and a photo detector 33. The reaction between the ligand and analyte can be recognized as a change of a resonance angle, which is an angle of incidence of light received by the interface 13b. To this end, the illuminator 32 is caused to apply light to the interface 13b at various values of angles of incidence satisfying a condition of the total reflection. The illuminator 32 includes a light source device 34 and an optical system 36, which includes a condensing lens, a diffusing plate and a polarizer. A position and angle of the installation of those elements are so determined that an angle of incidence of the light satisfies the condition of the above total reflection.

Examples of the light source device 34 include a light emitting diode (LED), laser diode (LD), super luminescent diode (SLD), and other light emitting element. A single element is used as the light source device 34 as a point light source, to illuminate the interface 13b. The diffusing plate diffuses light from the light source device 34, and suppresses onset of irregularity in the light amount. The polarizer allows only p-polarized light to pass, the p-polarized light creating the surface plasmon resonance. Note that no polarizer is required if directions of rays emitted by the light source device 34, for example an LD, are kept equal. However, a diffusing plate may be combined with the light source device 34 of a type of which directions of emitted rays are kept equal. Directions of rays in polarization are changed unequal by the passage through the diffusing plate. For this structure, the polarizer can be utilized to set equal the directions of the rays. The light obtained after the diffusion and polarization is condensed by a condensing lens, and directed to the prism 14. It is possible to travel rays with various angles of incidence toward the interface 13b without irregularity in the intensity.

The photo detector 33 receives light reflected by the interface 13b of the thin film 13, and detects intensity of the light. Rays of light are incident upon the interface 13b at various angles. The light is reflected by the interface 13b at various angles of reflection according to the angles of the incidence. The photo detector 33 receives the light at various angles of the reflection. An example of the photo detector 33 is a CCD area sensor or an array of photo diodes, which receives light reflected by the interface 13b at various angles of reflection, and photoelectrically converts the light into an output of SPR. The photo detector 33 outputs and sends an SPR signal to the data analyzer 8.

The sensing surface of the linker film 22 includes the measuring region 22a and the reference region 22b. On the basis of the measuring region 22a, the photo detector 33 outputs an SPR signal as a measuring signal. On the basis of the reference region 22b, the photo detector 33 outputs an SPR signal as a reference signal.

For the assay in the assay apparatus 6, at first, liquid buffer is introduced into the flow channel 16, and caused to flow continuously for a prescribed time. After this, analyte solution or analyte fluid 48, as a fluid which contains analyte and fluid medium that may be solvent, is introduced into the flow channel 16. Then liquid buffer is introduced again. Note that the flow channel 16 may be cleaned or washed before initially introducing the liquid buffer. Reading of data in the photo detector 33 starts upon initially introducing the liquid buffer in order to detect a reference level of a signal. The reading is continued until the introduction of the liquid buffer at the second time after entry of analyte fluid 27. It is possible not only to detect the reference level but to assay interaction or reaction between the analyte and the ligand, and to measure a signal until dissociation between the analyte and ligand in response to introduction of the liquid buffer.

Various liquids are available for use as the liquid buffer for assay, and solvent or diluent for the analyte fluid 27. Examples of the liquids include buffer liquids, or physiological saline water and other aqueous solutions of physiological salts, and pure water. It is possible according to a type of a ligand or analyte to determine suitably solution types and pH values of the solutions, and types of substances to be mixed, and their density. To facilitate dissolving of the analyte, dimethyl sulfo-oxide (DMSO) can be added to the physiological saline water. The use of the DMSO considerably influences to a level of an output signal. The buffer for assay is used for detecting the reference level of the signal, as described above. If DMSO is contained in the fluid for the analyte, it is preferable to use buffer for assay at a DMSO density approximately equal to that of the fluid in the analyte.

In general, the analyte fluid 27 may be kept preserved for a long time, for example one (1) year. It is likely that a difference occurs between an initial level and a current level of the DMSO density owing to a change with time. If assay with high precision is required, such a difference in the density is estimated according to the reference signal (ref-signal) level upon introducing the analyte fluid 27, so that measured data can be compensated for by DMSO density compensation.

Compensation data for the DMSO density compensation is obtained before introducing the analyte fluid 27. A plurality of liquid buffers different in the DMSO density are introduced to the flow channel 16. Amounts of changes in the levels of ref-signal and act-signal are evaluated so as to obtain the compensation data.

The interaction between the ligand and analyte is recognized as information of shifting of a position of attenuation of the reflected light on the photo reception surface of the photo detector 33. A refraction index of the thin film with the sensing surface 13a of the linker film becomes different between the states before and after the contact of the ligand with the analyte. Thus the resonance angle at which surface plasmon resonance occurs changes between those states. When reaction starts by the contact between the analyte and ligand, the resonance angle starts changes, to start shifting the attenuation position of the reflected light on the photo reception surface. A characteristic and other information of the analyte is determined by the assay apparatus 6, which sends the SPR output of the information to the data analyzer 8.

Note that in FIG. 4, the illuminator 32 and the photo detector 33 in the optical assay unit 31 are positioned so that a direction of light projected and reflected between those intersects horizontally with a flow of the flow channel 16, which is unlike the structure depicted in FIG. 5B. The state of FIG. 5B is simplified for the convenience. However, in the invention the illuminator 32 and the photo detector 33 may be positioned according to in FIG. 5B so that a direction of light projected and reflected between those is horizontally aligned with the flow of the flow channel 16 between the pipettes.

In the data analysis, the SPR signal output by the assay apparatus 6 is analyzed by the data analyzer 8, for quantitatively analyzing characteristics of the analyte. The data analyzer 8 is constituted by a personal computer, workstation or other electronic equipment, and analyzing software installed in such equipment.

The data analyzer 8 effects data analysis by obtaining a difference or ratio of the act-signal and ref-signal output by the assay apparatus 6. For example, the data analyzer 8 obtains data of a finite difference between the act-signal and ref-signal, and analyzes various items according to the finite difference. This makes it possible to cancel electric noise caused by external irregularities, such as individual specificity of the sensor unit 12 or the linker film 22, mechanical changes of the assay apparatus 6, temperature changes of the liquid, and the like. A signal with a high S/N ratio can be obtained.

According to the sensor unit 12, the flow channel device 41 or multi-channel flow cell is constituted from the device body part 58 of a rigid material, and the projecting sealant portion 56a more elastic than the device body part 58. Thus, the prism 14 can be kept fluid-tight by the projecting sealant portion 56a when the fastener block 42 is secured for the retention. Offsetting and deformation of the flow channel 16 can be prevented owing to the device body part 58.

Also, the combination of the device body part 58 and the soft elastic layer 56 is formed by the two color molding. Thus, no adhesion between those is required. Various failures due to an error in the adhesion can be prevented, including leakage of fluid, unwanted mixture of adhesive agent, solvent and the like to the sample fluid.

In the above embodiments, the projecting sealant portion 56a is one portion included in the soft elastic layer 56 inside the flow channel 16. However, the projecting sealant portion 56a can be initially separate from a base of the soft elastic layer 56, and may be secured to the same subsequently. Also, the base of the soft elastic layer 56 can be omitted because a fluid tight feature of the flow channel 16 can be obtained only by the projecting sealant portion 56a. However, the extension of the soft elastic layer 56 in the entire inner surface of the flow channel 16 from the projecting sealant portion 56a is advantageous, because the introduction of a fluid can be ensured by preventing leakage or other failure in connected portions between parts. Also, the extension of the soft elastic layer 56 can raise the moldability of the material of the soft elastic layer 56 because of its larger area of molding. The soft elastic layer 56 can be durable as prevented from peeling away from the device body part 58 as molded portions at the same time.

In the above embodiment, the device body part 58 is formed from resin. Instead of this, the device body part 58 can be a part of metal. This is effective in that the control of the temperature of the flow channel device 41 can be facilitated.

Note that the two color molding of the above embodiment cannot be used when the device body part 58 is a metal part. Instead, the insert molding can be preferably used to produce a composite unit including the device body part 58 and the soft elastic layer 56. In the insert molding, a metal part is initially prepared and set inside a mold. Then resin is injected into the mold, and solidified in a state wrapping the metal part, so as to obtain the composite unit.

Figure 6:
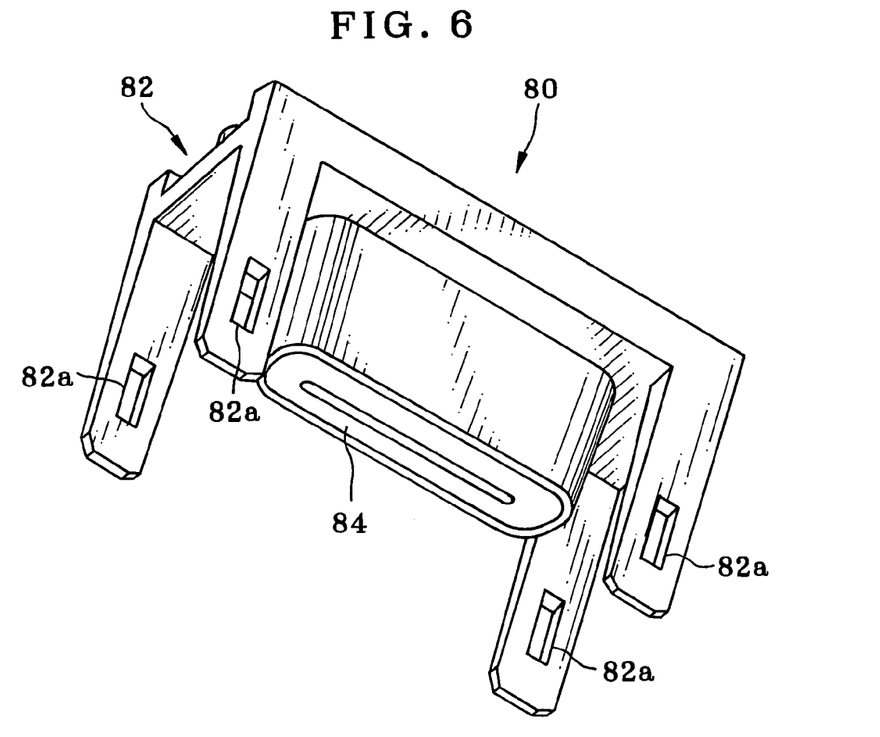
FIG. 6 is a perspective view illustrating another preferred flow channel device.
Figure 7:
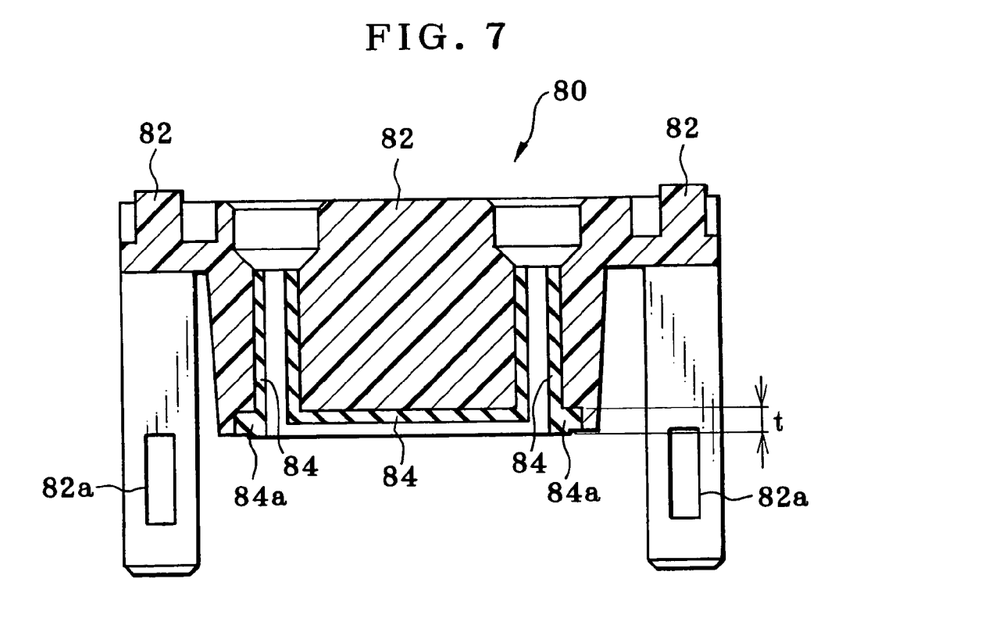
FIG. 7 is a cross section illustrating the flow channel device.

In contrast with the above embodiment where the fastener block 42 is used to keep contact between the flow channel device 41 and the prism 14, another preferred embodiment of FIGS. 6 and 7 of a flow channel device 80 has a fastening portion 82a. A rigid device body part 82 includes the fastening portion 82a for engagement with the fastening claws 14a of the prism 14. The fastening portion 82a is formed from the rigid material, and included in one piece of the rigid device body part 82. It is possible to keep the prism 14 in contact with the flow channel device 80 by loading of the flow channel device 80 on the prism 14. Also, a soft and elastic layer or coat 84 is overlaid on the device body part 82. A projecting sealant portion 84a is included in the soft elastic layer 84 together with a coating overlaid on the inner surface. The projecting sealant portion 84a extends in a flange shape on a lower face of the device body part 82, and contacts an upper surface of the prism 14. A depth or thickness t of the projecting sealant portion 84a can be equal to or more than 0.1 mm and equal to or less than 1.0 mm.

In addition to the SPR sensor, an assay sensor unit according to the invention can be other sensor in utilizing attenuated total reflection. One example of sensor unit according to utilizing the attenuated total reflection is a leaky mode sensor. The leaky mode sensor includes a dielectric medium, a cladding layer overlaid on the dielectric medium, and an optical waveguide layer overlaid on the cladding layer, those layers constituting a thin film. A first surface of the thin film is a sensing surface on the optical waveguide layer. A second surface of the thin film is a metal/dielectric interface on the cladding layer. When light becomes incident on the metal/dielectric interface to satisfy the condition of the total reflection, part of the light passes through the cladding layer, and enters the optical waveguide layer. A guided mode to propagate light is excited responsively in the optical waveguide layer, to attenuate the reflected light on the metal/dielectric interface. An angle of the incidence at which the guided mode is excited is changeable according to the refraction index of the medium positioned on the sensing surface. This is similar to the characteristic of the resonance angle of the SPR sensor. The attenuation of the reflected light is detected, so that it possible to measure the interaction on the sensing surface.

Note that any suitable material and form can be used for sealing between a device body part of the flow channel device and the prism 14 by utilizing various techniques in the field of the gasket for sealing.

The flow channel device or the sensor unit according to the invention may be any flow channel device or sensor unit in a system for assay or measuring different from that in utilizing attenuated total reflection if the system for assay or measuring is for chemical or biochemical analysis of biomaterials or samples and their interaction. Also, samples for assay may be any substances distinct from biomaterials. Examples of uses in other assay systems are suggested in U.S. Pat. No. 4,366,241 (corresponding to JP-A 57-063454), U.S. Pat. Nos. 4,440,497 and 5,064,287.

Although the present invention has been fully described by way of the preferred embodiments thereof with reference to the accompanying drawings, various changes and modifications will be apparent to those having skill in this field. Therefore, unless otherwise these changes and modifications depart from the scope of the present invention, they should be construed as included therein.

What is claimed is:

1. A flow channel member comprising:
   a body having a first surface which contacts a sensing surface for detecting reaction of a sample, and a second surface;
   a flow recess provided in said body having at least one edge portion which covers said sensing surface, thereby forming a flow channel between the first and the second surface to let a sample fluid of said sample flow on said sensing surface;
   wherein said flow channel member further comprises a coating layer, formed from a soft elastic material having a small non-specific adsorption, disposed on the inner wall of said flow recess, and wherein the body is made of a more rigid material than said soft elastic material;
   wherein said coating layer comprises a projecting sealant portion which extends beyond the edge portion of said body, and is resiliently deformed by the contacting pressure between said sensing surface and said body, thereby sealing said flow channel;
   wherein said body and said coating layer are integrally formed together by two color molding; and
   wherein said rigid material is a first resin and said soft material is a second resin.

2. The flow channel member as defined in claim 1, wherein said projecting sealant portion has a thickness equal to or more than 0.1 mm and equal to or less than 1.0 mm.

3. The flow channel member as defined in claim 1, further comprising first and second orifices provided at the second surface of said body, wherein said flow channel is in a substantially U-shape.

4. The flow channel member as defined in claim 1, wherein said soft material is amorphous polyolefin elastomer, and said rigid material is crystalline polyolefin.

5. The flow channel member as defined in claim 1, wherein said flow channel and said sensing surface are adapted for assay of said sample by utilizing attenuated total reflection, and said sensing surface is constituted by a prism.

6. A flow channel member comprising:
   a body having a first surface which contacts a sensing surface for detecting reaction of a sample, and a second surface;
   a flow recess provided in said body having at least one edge portion which covers said sensing surface, thereby forming a flow channel between the first and the second surface to let a sample fluid of said sample flow on said sensing surface;
   wherein said flow channel member further comprises a coating layer, formed from a soft elastic material having a small non-specific adsorption, disposed on the inner wall of said flow recess, and wherein the body is made of a more rigid material than said soft elastic material;
   wherein said coating layer comprises a projecting sealant portion which extends beyond the edge portion of said body, and is resiliently deformed by the contacting pressure between said sensing surface and said body, thereby sealing said flow channel;
   wherein said body and said coating layer are integrally formed together by insert molding; and
   wherein said rigid material is a metal and said soft material is a resin.

7. A flow channel member as defined in claim 6, wherein said projecting sealant portion has a thickness equal to or more than 0.1 mm and equal to or less than 1.0 mm.

8. A flow channel member as defined in claim 6, further comprising first and second orifices provided at the second surface of said body, wherein said flow channel is in a substantially U-shape.

9. flow channel member as defined in claim 6, wherein said soft material is amorphous polyolefin elastomer.

10. The flow channel member as defined in claim 6, wherein said flow channel and said sensing surface are adapted for assay of said sample by utilizing attenuated total reflection, and said sensing surface is constituted by a prism.

* * * * *